United States Patent [19]
Ullah et al.

[11] Patent Number: 6,066,336
[45] Date of Patent: May 23, 2000

[54] CHOLESTEROL-LOWERING TABLETS

[75] Inventors: Ismat Ullah, Cranbury; Gary James Wiley, Jackson, both of N.J.

[73] Assignee: Bristol-Myers Squibb Company, Princeton, N.J.

[21] Appl. No.: 09/131,970

[22] Filed: Aug. 11, 1998

Related U.S. Application Data

[60] Provisional application No. 60/060,357, Sep. 29, 1997.

[51] Int. Cl.⁷ .................................. A61K 9/36; A61K 9/30
[52] U.S. Cl. ...................... 424/480; 424/482; 424/475; 424/483; 424/465
[58] Field of Search ..................................... 424/474, 480, 424/464, 465, 78.12, 482, 483

[56] References Cited

U.S. PATENT DOCUMENTS

| | | |
|---|---|---|
| 4,843,098 | 6/1989 | Shaw et al. . |
| 4,895,723 | 1/1990 | Amer et al. . |
| 5,091,175 | 2/1992 | Imondi et al. . |
| 5,372,823 | 12/1994 | Bequette et al. . |
| 5,409,950 | 4/1995 | Dawson et al. . |
| 5,447,726 | 9/1995 | Nomura . |
| 5,455,047 | 10/1995 | Bequette et al. . |
| 5,468,727 | 11/1995 | Phillips et al. . |

*Primary Examiner*—Thurman K. Page
*Assistant Examiner*—Amy E. Pulliam
*Attorney, Agent, or Firm*—Richard P. Ryan

[57] ABSTRACT

An improved cholesterol-lowering tablet is manufactured by blending tablet grade cholestyramine with an appropriate amount of lubricant and directly compressing into elongated tablets having a specified thickness. These inner tablets are successfully film coated using aqueous film-coating processes without tablet preheating and by simultaneous spray-drying.

16 Claims, No Drawings

CHOLESTEROL-LOWERING TABLETS

CROSS REFERENCE TO RALATED APPLICATION

This non-provisional application claims the benefit of U.S. provisional application 60/060,357 filed Sep. 29, 1997.

FIELD OF THE INVENTION

The invention is concerned with improved tablets comprising ion exchange resins which have bioaffecting properties and the process for production of the tablets. Specifically, it deals with a process of producing aqueous film-coated cholestyramine resin tablets, which are improved in that they have the cholesterol lowering advantages of prior art cholestyramine tablets, but do not have the unpalatable mouth feel and swallowing difficulties of previous tablets.

BACKGROUND OF THE INVENTION

Cholestyramine, or colestyramine, is an antihyperlipoproteinemic ion exchange resin. It is a very hydrophilic polymer, whose typified structure of main polymeric groups is:

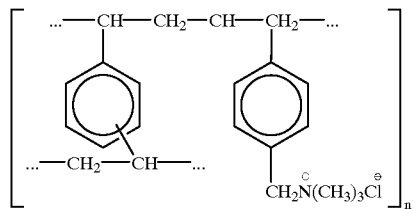

Cholestyramine and similar ion exchange resins, such as colestipol, lower cholesterol by attracting and agglomerating bile acids in the intestinal tract. Once agglomerated, the acids are excreted in feces, and serum LDL levels are lowered. Thus, cholesterol-lowering ion exchange resins are given orally such as in the form of a suspension, confection or a tablet. However, tablets must disintegrate readily so that the resin can act in the intestines.

Although cholestyramine is not water soluble, it rapidly absorbs available moisture, including atmospheric moisture, and swells or softens. This tendency to absorb moisture has led to problems in preparing and administering tablets of cholestyramine. The uncoated tablets are unpalatable and difficult to swallow. The tablets tend to disintegrate in the mouth while swallowing, adding to the unpleasant taste and causing a dry mouth and/or throat that inhibits swallowing. Also, it is well known that resins such as cholestyramine have an inherent unpleasant taste and odor. For these reasons, it is advantageous that the cholestyramine tablets have an adequate coating in order to allow swallowing, without objectionable taste and tablet disintegration in the mouth and/or throat.

The process for aqueous film coating of cholestyramine tablets is problematic because the resin readily absorbs moisture during the coating process. This causes tablets to swell and to undergo disintegration and surface erosion. Due to this moisture problem, the disclosure of U.S. Pat. No. 5,372,823 considered aqueous film coating of cholestyramine tablets to be impractical.

Attempts to film coat using a non-aqueous film-coating process were also found to be unsuccessful for cholestyramine, as the resin absorbed and retained unacceptably high levels of non-aqueous solvents as described in U.S. Pat. No. 5,372,823.

Several methods for avoiding these coating problems have been advanced.

Bequette, et at. in U.S. Pat. No. 5,372,823 and 5,455,047 describe the direct compression of cholestyramine powder into agglomerated cores which are then coated with a mixture of stearic acid and polyethylene glycol.

U.S. Pat. No. 4,843,098 to Shaw, et al. deals with cholestyramine resin formulations in which the "pre-swelled" resin is coated with hydrocolloid.

The hydrocolloid may be hydroxypropyl methycellulose. However, these preswelled resin formulations add to the weight and size of the tablets. Since 4–8 g doses of cholestyramine, given twice daily, are required, these large-sized, higher-weight tablets are undesirable as the dose must be taken as either hard-to-swallow larger tablets or a large number of smaller tablets. This adds to the problems of dose management and compliance.

Amer, et al. in U.S. Pat. No. 4,895,723 dealt with the production of a solid cholestyramine product. During processing the resin is blended with a syrup containing hydroxypropylmethylcellulose. That syrup forms a paste or dough from which a power can be made. Again, due to the considerably increased bulk, the cholestyramine formulations of Amer are best given by incorporation into a confection or beverage type of product formulation.

U.S. Pat. No. 5,447,726 of Nomura disclosed the tableting of 2-methylimidazole-dichloro-hydrin copolymer resin (MCI-196). MCI-196 is a cholesterol-lowering ion exchange resin whose general structural formula is:

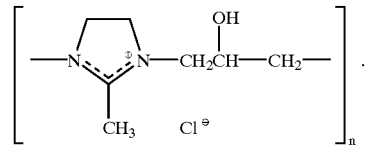

Inner tablets for coating are prepared by blending MCI-196 with hydroxypropylmethylcellulose in the presence of 14–20% by weight of water and up to 2% hydrated silica to make a granulate; mixing with lubricant; and then compressing. The disclosure emphasizes that at least 14% water must be added to MCI-196 in order to insure that the aqueous cellulosic coating will adhere to the resin. Nomura's tablets contain from 2–5% by weight of coating material comprised of hydroxypropylmethylcellulose, titanium oxide, talc and polyethylene glycol.

In U.S. Pat. No. 5,091,175, Imondi, et al. describe the enclosing of ion exchange resins with a non-degradable cellulosic coating to provide a semipermeable coat. The nature of the coating permits bile acids to react with the resin but prevents larger molecules from contacting and binding to the resin.

Tablets produced by these procedures have certain drawbacks. Some of these tablets are difficult to swallow. Waxy coatings on cholestyramine tablets become brittle and tend to chip. Once atmospheric moisture penetrates the chipped coating, cracks form when the hydrophilic resin swells. Subsequently, the tablet coating layer dissolves or disintegrates in a person's mouth, causing the hydrophilic ion exchange resin to come in contact with moist tissues of the oral cavity. In these instances, "gagging," "cotton mouth" or "dry mouth" resulted, leading to compliance problems. Further, waxy-coated tablets in general provide a weak coat that is non-expandable, inherently porous and whose film coat integrity is very temperature dependent. Thus, waxy coatings are generally not acceptable.

In addition, the large daily dose required for cholestyramine (from 4–8 g twice a day) gave rise to tablets containing 1 g of resin in order to make fewer units to swallow. The size of these tablets made them difficult to swallow. While 1 g tablets were preferred, the combination of their size and the failure to effectively prevent disintegration in the mouth/throat while swallowing gave rise to reports of patient choking.

It became clear that a reduction in tablet size and development of a new method of tablet coating of cholestyramine or other hydrophilic ion exchange resins was needed. Ideally, this method would overcome problems affecting compliance and contribute to easy-to-swallow tablets. The tablets should be smaller in size and of a shape making them easy to swallow. It would also be required that such tablets do not disintegrate in the mouth or throat during swallowing but disintegrate readily in the stomach after being swallowed.

It is the general object of this invention to make an easy-to-swallow tablet of an orally administrable cholesterol-lowering resin such as cholestyramine. In this regard, specific objectives are:

smaller sized tablets,
containing mainly resin to minimize the number of tablets that must be taken,
easy-to-swallow tablet shape,
tablet intact during swallowing,
tablet readily disintegrates in the stomach, and
tablet stable under the temperature and humidity conditions commonly encountered in pharmaceutical production, shipping and storage.

It is a further objective to develop a manufacturing process for preparation of the improved cholestyramine tablets that incorporates not only efficiencies of materials and processing steps, but also minimizes tablets with coating defects. Such a process would provide tablets maximizing the resin content and minimizing tablet excipients.

There is nothing in the prior art that discloses or suggests the novel combination of tablet formulation modifications that produce the improved, easy-to-swallow tablets of orally administrable cholesterol-lowering resin of this invention.

SUMMARY OF THE INVENTION

The invention deals with easy-to-swallow, cholesterol-lowering tablets containing a high weight percentage of a bile-acid sequestering resin such as cholestyramine; and a process for producing them. The selection of process materials, specifications, and operating steps are critical in producing the improved oral tablets of this invention. Drying raw cholesterol to a moisture content of about 9–12% by weight and then blending with a critical amount of tablet lubricant prior to directly compressing elongated cylindrical-shaped tablets to a selected thickness provides stress-free, hard tablets for film coating. Avoidance of tablet pre-heating during coating allows the use of aqueous film-coating processes employing simultaneous spray-drying to produce an easy-to-swallow tablet that remains intact in a patient's mouth and throat but that completely disintegrates after swallowing.

DETAILED DESCRIPTION OF THE INVENTION

By the novel and non-obvious selection of certain process materials and parameters, the improved, easy-to-swallow bile acid sequestering resin tablets of the instant invention are produced. In the tableting method, raw, commercial grade cholestyramine is used. It is appreciated that other similar cholesterol-lowering resins could be employed but cholestyramine is the preferred resin in this instance. The raw cholestyramine is usually supplied as tiny spheres of 2–3 mm in size and filled with water, generally containing 40–50% by weight of water.

In the present process the commercial grade cholestyramine, as received from the supplier, is dried to a moisture content of about 9–12% to provide tablet grade resin. Standard pharmaceutical drying processes can be used; however, a fluid bed drying process is preferred. This bulk tablet grade cholestyramine is then blended with a lubricant. No additional water is added for moisture adjustment prior to blending. For making older cholestyramine tablets, adjustment of the cholestyramine moisture level prior to compression was a critical process parameter. In the present process it can be ignored. This bulk cholestyramine is compactable, non-abrasive and free-flowing and is used without the addition of hydrocolloids, granulating agents, silicon dioxide, other excipients, or further drying or moisturizing. Due to the amount of resin required for effectiveness (4 or more g twice a day), tablet excipients, carriers and additives are to be minimized in order to keep the number and/or size of tablets to be taken at each dosing interval to a minimum.

The level of tablet lubricant employed has been found to be a critical factor in successful production of these tablets. Too little lubricant causes internal tablet stresses during compression and results in loss of structural integrity and premature tablet disintegration. Tablets with internal stresses that were subsequently film coated were found to develop cracks above the stress points when exposed to conditions of high humidity, e.g. 75% relative humidity. Magnified observation of tablets revealed these internal stresses by the presence of fine fissures on tablet surfaces.

Too much lubricant prevents the achievement of tablet hardness and this also causes tablet breakdown. Tablets of insufficient hardness could not be successfully film coated. The levels of lubricant to be blended is in the range of from about 0.05 to about 0.50% by weight. The preferred lubricant is magnesium stearate at a level of about 0.10–0.30% by weight in the resin-lubricant blend. The preferred level is about 0.15 to 0.20%. The blending can be done in blending apparatus commonly used for pharmaceutical formulation, e.g. a tumbling-type blender works well. Best results were obtained with short blending times, e.g. on the order of 10–15 minutes in tumbling-type blenders.

The resin-lubricant blend, preferably cholestyramine-magnesium stearate, is then directly compressed into suitably sized and shaped tablets to permit easy swallowing. The tablet size found most acceptable provided from 500 to 800 mg of cholestyramine binding activity (calculated on an anhydrous cholestyramine basis). For facilitating swallowing, generally elongated, cylindrical shaped tablets were selected. Capsule, oval or football shapes are preferred with a football-shaped tablet being most preferred. For the blend formulations of the present process, i.e. where the lubricant to resin ratio is within the selected guidelines, the punch type used for making the tablets does not matter.

An aspect of shape-size selection concerns another important and non-obvious aspect of this invention. Typically, pharmaceutical tablets are compressed to a desired tablet hardness. The preferred degree of tablet hardness dictates what the tablet thickness will be. In most cases, tablet thickness is not a critical parameter in dosage form development. For cholestyramine tablets, the thickness and overall size is a critical feature. In the present invention, compression to a specified tablet thickness and a constant tablet size is important. For the instant tablets, hardness is not used as a compression guide.

With respect to thickness, the resin content and selected tablet shape determines tablet thickness. As general examples of the improved tablets of this invention, the following dimensions are preferred.

| Tablet Shape | Resin Content | Tablet Dimensions (inches) | Concavity (inches) | Thickness (inches) |
| --- | --- | --- | --- | --- |
| Football | 500 mg | 0.62 × 0.27 | 0.05 | 0.70 |
| Football | 800 mg | 0.73 × 0.36 | 0.06 | 0.83 |

The uncoated tablets are produced in a tablet press or other standard pharmaceutical tablet compression apparatus familiar to one skilled in the art. Typically, tablet grade cholestyramine is blended with about 0.17% by weight of magnesium stearate in a tumbling-type blender for about 10–12 minutes. The resulting blend is then compressed on a rotary tablet press to target thickness for the selected weight.

The final operation to produce the easy-to-swallow tablets is aqueous film coating. Earlier attempts to use aqueous film coating for bulk cholestyramine tablets were unsuccessful. Nomura reports successful aqueous film coating of MCI-196, a different resin, by incorporation of 14% water, hydroxymethylpropylcellulose, a lubricant, and 2% silicon dioxide in the resin blend to be film coated.

In the present invention, aqueous film coating of the uncoated compressed cholestyramine tablets was successful due to the discovery that by avoiding the standard tablet preheating operation prior to film coating and by using drying with the coating application, stable and durable coating could be achieved. The successful effect achieved by avoiding tablet preheating was unexpected since it is standard practice to inhibit moisture/solvent absorption by the uncoated tablet by preheating them prior to film coating. Commonly, if the unfinished tablet absorbs moisture, the tablet surface undergoes erosion and the film coat will not adhere properly to the tablet surface causing failure of the film-coating process. As would be evident, this tendency is even more pronounced for unfinished tablets which are moisture sensitive or, like cholestyramine, have an affinity for moisture. Therefore, it would be expected that preheating is a necessary part of the film-coating process for tablets like cholestyramine. As part of the present invention it was discovered that surface erosion for the uncoated cholestyramine tablets was proportional to the length and intensity of the preheating process. Subsequent experimentation demonstrated that unwarmed, uncoated tablets could be successfully coated by an aqueous film-coat process if the spraying and drying processes were done simultaneously.

Prior to the coating operation it is important that the uncoated tablets be kept at room temperature in closed containers and not be heated/dried prior to the aqueous film-coating process. By combining and balancing the spraying and drying processes in the film-coating operation, any moisture absorbed by the inner tablet appears to have little effect on tablet and coating stability.

The aqueous film-coating process comprises the use of an aqueous solution or suspension of a coating polymer and optional amounts of a plasticizer and an antifoam agent. While most coating polymers used in aqueous film-coating operations would be applicable, aqueous cellulosic or acrylic polymers would be favored. A hydroxyalkyl cellulose and in particular, hydroxypropyl methylcellulose, is preferred. Mixtures of coating polymers can also be used. A suitable plasticizer, e.g. polyethylene glycol, can also be incorporated into the solution or suspension. Additionally, an antifoam agent such as an emulsion of antifoam C can be added to the filmcoat suspension/solution. Preferred filmcoat preparations are comprised of hydroxypropyl methylcellulose, polyethylene glycol and an antifoam agent. It is most preferred to use commercially available film-coating formulations such as OPADRY® (from Colorcon Corporation) or DRYCLEAR® (from Cromptom Knowles Corporation). To these are added antifoam emulsions such as Antifoam C Emulsion. The most preferred film-coating formulation is OPADRY® CLEAR (Colorcon) which is formulated with low viscosity hydroxypropyl methylcellulose and polyethylene glycol (PEG) 6000 and PEG 400 as plasticizers. Antifoam C Emulsion is used with the OPADRY® as an antifoam agent and as a self-polishing agent in the tablet coat. The viscosity of this aqueous film coat suspension containing 2% polymer is less than 8 c St. at 20° C.

Use of these polymer coat formulations avoids the use of additional solids such as talc or titanium oxide in the suspension and seals the inner tablet without requiring a tablet subcoat. Generally, the aqueous solution/suspension is comprised of from about 5 to about 15% of total solid contents. The preferred solution/suspensions contain about 10% polymer-plasticizer and about 1 % antifoam emulsion. It is contemplated that for certain applications minor amounts of nonaqueous solvents or carriers could be used.

The film-coating process is done employing conventional tablet coating equipment such as the Accela Cota device. The coating process uses drying temperatures in the range of about 50–70° C. A typical coating operation consists of coating the inner tablets, without preheating, using pan coating or fluid bed coating equipment suited to conventional aqueous film-coating processing. Film coating is applied to provide a 6–12% weight gain, preferably about 8%, for the tablet. Process parameters for the aqueous film coating of the compressed cholestyramine tablets are adjusted so that adequate drying prevents significant moisture penetration into the tablet. Residual moisture is removed by drying at the completion of the coating operation.

Reasonable variations in the coating process can be made and these would be known to one skilled in the art. Modifications would be expected for the use of specific film-coating equipment and variations in tablet load. The elimination of tablet preheating, however, is critical to success of the coating operation. In practice the coating apparatus is brought to the desired coating temperature prior to introduction of the uncoated tablets. This prevents tablet heating that would occur during equipment warm-up. The spray-coating process is initiated as soon as the tablets are loaded. Tablet tumbling, liquid spray coating and drying are done simultaneously. The initial spray level is kept low to prevent moisture absorption by the raw tablet surface. After some surface coverage the spray rate can be increased and the drying rate balanced to achieve an efficient coating process. Using the film-coating process of this invention removes the problems defeating earlier attempts to film coat cholestyramine tablets. In the current process, if the compressed inner tablets are satisfactory, the final coated tablet will meet all of the objectives set forth above.

The novel process for production of the improved cholestyramine tablets is summarized in the following process steps.

1. Raw cholestyramine is dried to tablet grade bulk resin having a moisture content in the range of 9 to 12% by weight with 10–11% being preferred.

2. The tablet grade resin is blended with a suitable lubricant present in an amount representing about 0.01 to 0.5% of the blend by weight. The lubricant level is a critical parameter in achieving tablets that will maintain structural integrity throughout the coating process. Magnesium stearate at a level of 0.15–0.20% by weight is preferred. The blend is directly compressed into elongated, cylindrical shaped tablets. In the present invention the blend is compressed to a desired thickness instead of a target tablet hardness.

3. The final step comprises aqueous film coating of the unheated uncoated compressed tablet. Simultaneous spraying and drying allow the deposition of the polymer coat without significant moisture penetration of the tablet itself.

Tablets resulting from this process are of a size and shape that facilitates swallowing and the durable film coat remains intact while being taken orally but disintegrates in the stomach and intestines to provide efficient bile acid binding. By avoiding the addition of other components to the tablet, the resin load per tablet is maximized. This is an advantage when the required dosage levels are very large and multiple tablets must be ingested to reach the amount of drug necessary for effective reduction of cholesterol.

Thus, the novel process provides cholestyramine tablets meeting the general objective of being easy to swallow. This was achieved by meeting the specific objectives of this invention.

The tablets at 500 and 800 mg potency with only lubricant and coating are smaller in size but the resin content is maximized.

Cylindrical, elongated, football shaped tablets facilitate swallowing.

The tablets remain intact during swallowing but readily disintegrate in the stomach.

The film coat maintains its integrity under high humidity conditions.

The production of these improved tablets and advantages in manufacture and use will be more evident in light of the following examples which examples which are provided for guidance. It is understood that the examples are intended only to be instructive and not exclusive. Modifications of process steps and materials can be made without departing from the claimed invention. Such modifications would be evident to one skilled in the art.

SPECIFIC EMBODIMENTS

The Inner (Uncoated) Cholestyramine Tablet

Tablet grade bulk cholestyramine (prepared by drying raw commercial cholestyramine to a 9 to 12% moisture content) was used. A V-blender was loaded with the tablet grade cholestyramine (174.7 Kg) and magnesium stearate (0.29 Kg) and the contents blended for 10 minutes. The blend was removed from the V-blender and stored in polyethylene-lined fiber drums prior to tableting.

For tableting, the blend was compressed, e.g. on a BB2 27 station press, using a football-shaped die. The tablets were compressed to thickness providing tablet dimensions of 0.730×0.363 inches with a concavity of 0.61 inch. The uncoated tablets were stored in polyethylene-lined cardboard boxes until being film coated.

The Coated Cholestyramine Tablet

A film coating suspension was prepared using the following ingredients.

| Ingredient | Amount (Kg) |
| --- | --- |
| OPADRY ® CLEAR (YS-1-7472) | 100 |
| Antifoam C emulsion | 10 |
| Purified water, U.S.P. | 890 |
| Total | 1000 |

In general, the water was weighed into a stainless steel tank fitted with an overhead mixer run at medium speed. The antifoam C emulsion was added and mixing continued for about 5 minutes. The OPADRY® was slowly added to the stirred mixture and mixing continued until no lumps were visible in the suspension.

A 48 inch Accela-Cota film-coater was used for the coating process. The pan was set at 5–7 rpm and the apparatus was equilibrated by warming, using an inlet temperature of 55–60° C., until the outlet temperature reached 40–50° C. Pan rotation and heating were interrupted while the uncoated tablets (80 Kg of 800 mg potency tablets) were loaded into the pan. Pan rotation and heating were resumed and spraying, at the rate of 200–300 g coating suspension per minute, was started. The atomization pressure was in the range of 25–35 psi. After about 75 minutes the inlet temperature was raised to 65–70° C. and the spray pump was increased to about 400–500 g/minute. When about 10% by weight of coating was applied (about 86 Kg of the coating suspension sprayed), the spraying process was stopped and the inlet temperature was lowered to about 60° C. and pan speed reduced to about 5 rpm for a period of 10–15 minutes to complete drying. The coated tablets were stored in polyethylene-lined fiber drums, containing bags of silica and charcoal, until pharmaceutical packaging was done.

Cholestyramine Film-Coated Tablet, 800 mg (Anhydrous Weight)

Using the general procedure set forth above, 800 mg strength cholestyramine tablets were produced according to the following formulation.

| Ingredient | Amount per Unit Dosage Form | Commentary |
| --- | --- | --- |
| Cholestyramine for tableting (containing 10.5% moisture) | 0.89385 g | — |
| Magnesium stearate | 0.00150 g | (can be increased to about 0.27% by weight in the uncoated tablet) |
| Total weight | 0.89535 g | (will vary as amount of lubricant varies) |

2. Film coat (quantities are based on a 0% by weight film coat

| Ingredient | Amount per Unit Dosage Form | Commentary |
|---|---|---|
| OPADRY ® CLEAR (YS-1-7472) | 0.09640 g | — |
| Antifoam C emulsion | 0.00308 g | (based on average non-volatile contents of 32%) |
| Purified water, U.S.P. | 0.85626 g | — |
| Total tablet weight | 0.99483 g | (can vary with differing levels of lubricant and film coat) |

We claim:

1. A process for production of easy-to-swallow tablets comprising the steps of
   a) drying raw cholestyramine to a moisture content of about 9 to 12% by weight;
   b) blending the dried cholestyramine of step a) with about 0.01 to 0.5% of a lubricant to prevent internal tablet stress and directly compressing elongated, cylindrically-shaped tablets to a desired thickness; and
   c) applying a protective film coating to the uncoated tablet using aqueous film coating comprising simultaneous spray-drying without preheating the inner tablet during the coating process.

2. The process of claim 1 wherein about 0.1 to 0.2% of magnesium stearate is the lubricant used in step b).

3. The process of claim 1 wherein the elongated, cylindrically-shaped tablets are compressed to a thickness of about 0.70 to 0.83 inches.

4. The process of claim 1 wherein the aqueous film coating process comprises the use of an aqueous solution or suspension of a coating polymer selected from an aqueous cellulosic or acrylic polymer.

5. The process of claim 4 wherein the coating polymer is a hydroxyalkylcellulose.

6. The process of claim 5 wherein the coating polymer is hydroxypropylmethylcellulose.

7. The process of claim 4 wherein the aqueous film coating process also uses a suitable plasticizer selected from polyethylene glycols.

8. The process of claim 4 wherein the aqueous film coating process also uses an antifoam emulsion.

9. The process of claim 6 wherein the aqueous coating process uses a solution or suspension of about 5 to 15% of solid contents comprised of hydroxypropylmethylcellulose, polyethylene glycol 6000, polyethylene glycol 400 and antifoam C emulsion.

10. The film-coated cholestyramine tablets produced by the process of one of claims 1 through 9.

11. An easy-to-swallow tablet comprised of
   an inner tablet comprising a cholesterol-lowering ion exchange resin having about 9 to 12% moisture and about 0.01 to 0.5% by weight of lubricant directly compressed to the desired thickness; and
   an outer aqueous film coat providing about 6 to 12% by weight of the easy-to-swallow tablet, the film coat comprising an aqueous cellulosic polymer with optional added amounts of a plasticizer and an antifoam emulsion.

12. The tablet of claim 1 wherein the ion exchange resin is cholestyramine.

13. The tablet of claim 2 wherein the lubricant is magnesium stearate and the cellulosic polymer is hydroxypropylmethylcellulose.

14. The tablet of claim 3 wherein the film coat also contains about one part of an antifoam agent per 10 parts hydroxypropylmethylcellulose.

15. The tablet of claim 3 wherein the inner tablet contains from about 0.1 to 0.2% of magnesium stearate.

16. The tablet of claim 1 wherein the film coat is comprised of hydroxypropylmethylcellulose, polyethylene glycol and an antifoam agent.

* * * * *